(12) United States Patent
Bonnert et al.

(10) Patent No.: US 7,741,360 B2
(45) Date of Patent: Jun. 22, 2010

(54) BI-ARYL OR ARYL-HETEROARYL SUBSTITUTED INDOLES

(75) Inventors: Roger Victor Bonnert, Loughborough (GB); Timothy Jon Luker, Loughborough (GB); John Cumming, Macclesfield (GB)

(73) Assignee: AstraZeneca AB (SE)

( * ) Notice: Subject to any disclaimer, the term of this patent is extended or adjusted under 35 U.S.C. 154(b) by 16 days.

(21) Appl. No.: 12/302,353

(22) PCT Filed: May 25, 2007

(86) PCT No.: PCT/GB2007/001951

§ 371 (c)(1),
(2), (4) Date: Nov. 25, 2008

(87) PCT Pub. No.: WO2007/138282

PCT Pub. Date: Dec. 6, 2007

(65) Prior Publication Data

US 2009/0143449 A1    Jun. 4, 2009

Related U.S. Application Data

(60) Provisional application No. 60/803,275, filed on May 26, 2006.

(51) Int. Cl.
A61K 31/405   (2006.01)
C07D 209/30   (2006.01)

(52) U.S. Cl. .................. 514/414; 514/418; 548/467; 548/484

(58) Field of Classification Search .................. None
See application file for complete search history.

(56) References Cited

U.S. PATENT DOCUMENTS

| | | | |
|---|---|---|---|
| 5,459,150 | A | 10/1995 | Brooks et al. |
| 5,486,525 | A | 1/1996 | Summers, Jr. et al. |
| 5,567,711 | A | 10/1996 | Sheppard et al. |
| 6,916,841 | B2 | 7/2005 | Seehra et al. |
| 6,933,316 | B2 | 8/2005 | Hsieh et al. |
| 7,166,607 | B2 | 1/2007 | Bonnert et al. |
| 2005/0222201 | A1 | 10/2005 | Birkinshaw et al. |
| 2006/0111426 | A1 | 5/2006 | Bonnert et al. |
| 2006/0264444 | A1 | 11/2006 | Bonnert et al. |
| 2008/0027092 | A1 | 1/2008 | Bonnert et al. |
| 2008/0051586 | A1 | 2/2008 | Keegan et al. |
| 2008/0249110 | A1 | 10/2008 | Bonnert et al. |
| 2009/0143449 | A1 | 6/2009 | Bonnert et al. |

FOREIGN PATENT DOCUMENTS

| | | |
|---|---|---|
| EP | 0254241 | 1/1988 |
| EP | 0530907 | 3/1993 |
| EP | 0576347 | 12/1993 |
| EP | 0 924 209 | 6/1999 |
| EP | 1170594 | 1/2002 |
| EP | 1505061 | 2/2005 |
| GB | 1356834 | 6/1974 |
| GB | 2422831 | 8/2006 |
| WO | WO 94/19321 | 9/1994 |
| WO | WO 95/16687 | 6/1995 |
| WO | WO 98/13368 | 4/1998 |
| WO | WO 99/09007 | 2/1999 |
| WO | WO 00/78761 | 12/2000 |
| WO | WO 01/032621 | 5/2001 |
| WO | WO 01/47922 | 7/2001 |
| WO | WO 01/92224 | 12/2001 |
| WO | WO 03/064387 | 8/2003 |
| WO | WO 03/066046 | 8/2003 |
| WO | WO 03/066047 | 8/2003 |
| WO | WO 03/097598 | 11/2003 |
| WO | WO 03/101961 | * 12/2003 |
| WO | WO 03/101981 | 12/2003 |
| WO | WO 2004/007451 | 1/2004 |
| WO | WO 2004/016609 | 2/2004 |
| WO | WO 2004/106302 | 12/2004 |
| WO | WO 2005/019171 | 3/2005 |
| WO | WO 2005/040114 | * 5/2005 |
| WO | WO 2005/054232 | 6/2005 |
| WO | WO 2006/075139 | 7/2006 |
| WO | WO 2007/138282 | 12/2007 |
| WO | WO 2007/140786 | 12/2007 |
| WO | WO 2008/000409 | 1/2008 |

OTHER PUBLICATIONS

Antonio R. Damasio, Alzheimer's Disease and Related Dementias, Cecil Textbook of Medicine, 20th edition (1996), vol. 2, pp. 1992-1996.*

FDA mulls drug to slow late-stage Alzheimer's [online], [retrieved on Sep. 23, 2003]. Retrieved from the Internet, URL: http://www.cnn.com/2003/HEALTH/conditions/09/24/alzheimers.drug.ap/indez.html, pp. 1 and 2.*

"COPD: Causes and Prevention." NIH SeniorHealth. National Heart, Lung, and Blood Institute. Accessed Apr. 6, 2009. <http://nihseniorhealth.gov/copd/causesandprevention/01.html>.*

(Continued)

Primary Examiner—Golam M. M. Shameem
Assistant Examiner—Alicia L Fierro
(74) Attorney, Agent, or Firm—Fish & Richardson P.C.

(57) ABSTRACT

The present invention relates to substituted indoles of Formula (I) useful as pharmaceutical compounds for treating respiratory disorders.

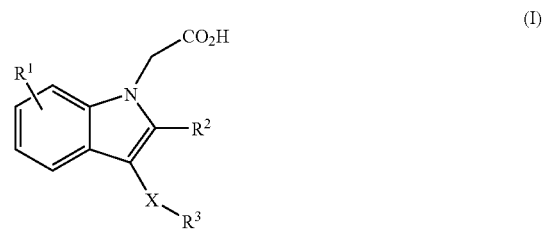

15 Claims, No Drawings

OTHER PUBLICATIONS

"Prevention of Cystic Fibrosis." WrongDiagnosis.com. Accessed Apr. 6, 2009. <http://www.wrongdiagnosis.com/c/cf/prevent.htm>.*

Morissette et al. "High-throughput crystallization: polymorphs, salts, co-crystals and solvates of pharmaceutical solids." Advanced Drug Delivery Reviews 2004, 56, 275-300.*

Vippagunta, Sudha R. "Crystalline Solids." Advanced Drug Delivery Reviews 48(2001): 3-26.*

STN International, CAPLUS accession No. 2001:338492, Document No. 134:353315, Wakunaga Pharmaceutical Co., Ltd., "Preparation of indole derivatives as chymase inhibitors and drugs containing the same as the active ingredient", & WO,A1,2001032621, 20010510, RN 64137-76-4, 336186-33-5.

STN International, CHEMCATS accession No. 2000:1027702, Apr. 26, 2001, 8004-3013, "1H-Indole-1-acetic acid, 2-methyl-3-(phenylthio)-, ethyl esther", CAS Registry No. 300860-50-8.

STN International, file CAPLUS, CAPUS accession No. 1995:401159, Document No. 122:187576, Yoshitomi Pharmaceutical Industries, Ltd., "Preparation of fused pyrazole derivatives", & JP,A2, 06206872, 19940726.

Vippagunta et al., abstract, "Crystalline solids", *Advanced Drug Delivery Reviews* 48:3-26 (2001).

Atkinson et al., "A New Synthesis of 3-Arylthioindoles", *Synthesis* 6:480-481 (1988).

Cecil Textbook of Medicine, 20th edition, vol. 2:1992-1996 (1996).

Cecil Textbook of Medicine, 20th edition, vol. 2:2050-2057 (1996).

FDA mulls drug to slow late-stage Alzheimer's [online], [retrieved on Sep. 23, 2003]. Retrieved from the Internet, URL:http://www.cnn.com/2003/HEALTH/conditions/09/24/alzheimers.drug.ap/indexhtml>.

Database CA 'Online! Chemical Abstracts Service, Columbus, Ohio, US; Tanimoto, Norihiko et al: "Preparation of indole derivatives as PGD2 receptor antagonists" XP002301963 retrieved from STN Database accession No. 2003:931327.

Garcia et al., "A Novel Synthesis of 3-Cyanoindoles and a New Route to Indole-3-Carboxylic Acid Derivatives", *Tetrahedron Letters* 26(15):1827-1830 (1985).

Hamel et al., "Regioselective Synthesis of Mixed Indole 2,3-Bis-(sulfides). A Study of the Mechanism of the Second Sulfenylation of Indole", *J. Org. Chem.* 61:1573-1577 (1996).

Hary et al., "Efficient synthesis of 3-(4,5-dihydro-1$H$-imidazole-2-yl)-1$H$-indoles", *Tetrahedron Letters* 42:5187-5189 (2001).

Howard et al., "Synthesis and aldose reductase inhibitory activity of substituted 2(1$H$)-benzimidazolone-and oxindole-1-acetic acids", *Eur J Med Chem* 27:779-789 (1992).

Lüscher et al., "Deblocking of $o$-Nitrophenylsulfenyl-Protected Peptides by Ammonium Thiocyanate and (2-Methyl-1-indolyl) acetic acid", *Helv. Chim. Acta* 66(2):602-605 (1983).

Matassa et al., "Evolution of a Series of Peptidoleukotriene Antagonists: Synthesis and Structure/Activity Relationships of 1,3,5-Substituted Indoles and Indazoles", *J. Med. Chem.* 33:1781-1790 (1990).

Matsugi et al., "An efficient sylfenylation of aromatics using highly active quinone mono $O,S$-acetal bearing a pentafluorophenylthio group", *Tetrahedron Letters* 42:1077-1080 (2001).

Matsugi et al., "Facile and Efficient Sulfenylation Method Using Quinone Mono-$O,S$-Acetals under Mild Conditions", *J. Org. Chem.* 66:2434-2441 (2001).

Morissette et al., "High-throughput crystallization: polymorphs, salts, co-crystals and solvates of pharmaceutical solids", *Advanced Drug Delivery Reviews* 56:275-300 (2004).

Ovenden et al., "Echinosulfonic Acids A-C and Echinosulfone A: Novel Bromoindole Sulfonic Acids and a Sulfone from a Southern Australian Marine Sponge, Echinodictyum", *J. Nat. Prod.* 62:1246-1249 (1999).

Patani and LaVoie, "Bioisosterism: A Rational Approach in Drug Design", *Chem Rev.* 96:3147-3176 (1996).

STN International, CAPLUS accession No. 1977:535057, Document No. 87:135057, Sankyo Co., Ltd., "3- Indolyl thio ethers", & JP,A2,52039671, 19770328, RN 64137-76-4, 54491-43-9, 56366-45-1.

STN International, CAPLUS accession No. 1980:6356, Document No. 92:6356, Gabrielyan, G.E. et al.: "Indole derivatives. LX. Synthesis of indole compounds with a furan ring", & Armyanskii Khimicheskii Zhurnal (1979), 32(4), 309-14, RN 51842-57-0.

STN International, CAPLUS accession No. 2001:235566, Document No. 134:266203, Kato, Susumu et al.: "Preparation and application of benzopyranone derivatives"; & JP,A2,2001089471, 20010403, RN 332082-10-7.

* cited by examiner

BI-ARYL OR ARYL-HETEROARYL SUBSTITUTED INDOLES

CROSS-REFERENCE TO RELATED APPLICATIONS

This application is a national phase application under 35 U.S.C. §371 of PCT International Application No. PCT/GB2007/001951, filed May 25, 2007, which claims the benefit of U.S. Provisional Application No. 60/803,275, filed May 26, 2006. Each of these prior applications is incorporated herein by reference in its entirety.

The present invention relates to substituted indoles useful as pharmaceutical compounds for treating respiratory disorders, pharmaceutical compositions containing them, and processes for their preparation.

EPA 1 170 594 discloses methods for the identification of compounds useful for the treatment of disease states mediated by prostaglandin D2, a ligand for orphan receptor CRTh2. GB 1356834 discloses a series of compounds said to possess anti-inflammatory, analgesic and antipyretic activity. WO2003101961, WO2004007452, WO2004106032, WO2005018529 and WO2005019171 disclose a series of mono-aryl or mono-heteroaryl substituted indole acetic acids which are active at the CRTh2 receptor. It has now surprisingly been found that certain bi-aryl or aryl-heteroaryl substituted indoles are active at the CRTh2 receptor, and as a consequence are expected to be potentially useful for the treatment of various respiratory diseases, including asthma and COPD.

In a first aspect the invention therefore provides a compound of formula (I) or a pharmaceutically acceptable salt or solvate thereof:

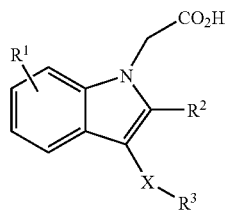

(I)

in which

X is O or $S(O)_n$ where n is 0, 1 or 2;

$R^1$ is hydrogen, halogen, CN, nitro, $S(O)_nR^4$, OH, $OR^4$, $OS(O)_nR^4$, $S(O)_nR^4$, $SO_2NR^5R^6$, $CONR^5R^6$, $NR^5R^6$, $NR^4SO_2R^5$, $NR^4CO_2R^6$, $NR^4COR^6$, $NR^4SO_2NR^5R^6$, $NHSO_2R^5$, $NHCO_2R^6$, $NHCOR^6$, $NHCONR^4$, $NHSO_2NR^5R^6$, aryl, heteroaryl, $C_2$-$C_6$ alkenyl, $C_2$-$C_6$ alkynyl, $C_3$-$C_8$cycloalkyl or $C_{1-6}$ alkyl, the latter four groups being optionally substituted by one or more substituents independently selected from halogen, $OR^8$, $NR^5R^6$ and $S(O)_nR^7$ where n is 0, 1 or 2;

$R^2$ is hydrogen, halogen, CN, $SO_2R^4$, $CONR^5R^6$, $CH_2OH$, $CH_2OR^4$, $C_{3-8}$cycloalkyl or $C_{1-7}$alkyl, the latter two groups being optionally substituted by one or more substituents independently selected from halogen, $OR^8$, $NR^5R^6$ or $S(O)_nR^7$ where n is 0, 1 or 2;

$R^3$ is aryl or heteroaryl each of which is optionally substituted by one or more substituents independently selected from hydrogen, halogen, CN, nitro, $S(O)_nR^4$, OH, $OR^4$, $OS(O)_nR^4$, $S(O)_nR^4$, $SO_2NR^5R^6$, $CONR^5R^6$, $NR^5R^6$, $NR^4SO_2R^5$, $NR^4CO_2R^6$, $NR^4COR^6$, $NR^4SO_2NR^5R^6$, $NHSO_2R^5$, $NHCO_2R^6$, $NHCOR^6$, $NHCONR^4$, $NHSO_2NR^5R^6$, aryl, heteroaryl, $C_2$-$C_6$ alkenyl, $C_2$-$C_6$ alkynyl, $C_3$-$C_8$cycloalkyl or $C_{1-6}$ alkyl, the latter four groups being optionally substituted by one or more substituents independently selected from halogen atoms, aryl, heteroaryl, $OR^8$, $NR^5R^6$ or $S(O)_nR^7$ where n=0, 1 or 2;

$R^4$ represents aryl, heteroaryl, $C_{3-8}$cycloalkyl or $C_{1-6}$alkyl all of which may be optionally substituted by one or more substituents independently selected from hydrogen, halogen atoms, aryl, heteroaryl, $OR^{10}$, $NR^{11}R^{12}$, $S(O)_nR^{13}$ (where n=0, 1 or 2), $CONR^{14}R^{15}$, $NR^{14}COR^{15}$, $SO_2NR^{14}R^{15}$, $NR^{14}SO_2R^{15}$, CN or nitro;

$R^5$ and $R^6$ independently represent a hydrogen atom, aryl, heteroaryl, $C_{3-8}$cycloalkyl or $C_{1-6}$alkyl, the latter two of which may be optionally substituted by one or more substituents independently selected from halogen atoms, aryl, heteroaryl, $OR^{10}$, $NR^{11}R^{12}$, $S(O)_nR^{13}$ (where n=0, 1 or 2), $CONR^{14}R^{15}$, $NR^{14}COR^{15}$, $SO_2NR^{14}R^{15}$, $NR^{14}SO_2R^{15}$, CN or nitro; or $R^5$ and $R^6$ together with the nitrogen atom to which they are attached can form a 3-8 membered saturated heterocylic ring optionally containing one or more atoms selected from O, $S(O)_n$ where n=0, 1 or 2, or $NR^{16}$, and itself optionally substituted by $C_{1-6}$ alkyl or $C_{3-8}$cycloalkyl;

$R^7$ and $R^{13}$ independently represent aryl, heteroaryl, $C_{3-8}$cycloalkyl and $C_{1-6}$alkyl, all of which may be optionally substituted by one or more halogen atoms, aryl, heteroaryl, $OR^{10}$, $NR^{11}R^{12}$, $S(O)_nR^{13}$ (where n=0, 1 or 2), $CONR^{14}R^{15}$, $NR^{14}COR^5$, $SO_2NR^{14}R^{15}$, $NR^{14}SO_2R^{15}$, CN or nitro;

$R^8$ represents a hydrogen atom, $C(O)R^9$, aryl, heteroaryl or $C_1$-$C_6$ alkyl (optionally substituted by one or more halogen atoms, aryl or heteroaryl);

each of $R^9$, $R^{10}$, $R^{11}$, $R^{12}$, $R^{14}$ and $R^{15}$ independently represents a hydrogen atom, $C_{3-8}$cycloalkyl, $C_1$-$C_6$ alkyl, an aryl or a heteroaryl group (all of which may be optionally substituted by one or more halogen atoms); and $R^{16}$ is hydrogen, $C_{1-4}$ alkyl, —$COC_1$-$C_4$ alkyl, $COYC_1$-$C_4$alkyl where Y is O, $S(O)_nR^{13}$ (where n=0, 1 or 2) or $NR^7$.

Provided that:
One or more of the substituents on $R^3$ must be aryl, heteroaryl or $C_{1-6}$alkyl (the latter group being substituted by aryl or heteroaryl);
When $R^3$ is biphenyl, X must be O or S;
When $R^3$ is aryl substituted by $C_{1-6}$alkyl, X must be O or S;
$R^3$ cannot be 4-phenyl-1,3-thiazol-2-yl.

In the context of the present specification, unless otherwise indicated, an alkyl or alkenyl group or an alkyl or alkenyl moiety in a substituent group may be linear, branched or cyclic.

Aryl is phenyl or naphthyl, preferably phenyl.

Heteroaryl is defined as a 5-7 membered aromatic ring or can be 6,6- or 6,5-fused bicyclic each ring containing one or more heteroatoms selected from N, S and O. Examples include but are not limited to pyridine, pyrimidine, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, 1,2-benzisothiazole, benzoxazole, purine, 4H-quinolizine, cinnoline, phthalazine, quinazoline, quinoxaline, 1,8-naphthyridine, pteridine, quinolone.

When $R^5$ and $R^6$ together with the nitrogen to which they are attached form a 3-8 membered saturated heterocyclic ring examples include but are not limited to morpholine, thiomorpholine, azetidine, imidazolidine, pyrrolidine, piperidine and piperazine. Substituents can be present on carbon or appropriate nitrogen atoms of such rings.

The term alkyl, whether alone or as part of another group, includes straight chain, branched or cyclic alkyl groups.

Except where otherwise stated aryl or heteroaryl groups can be optionally substituted by one or more substituents independently selected from hydrogen, halogen, CN, nitro, $S(O)_nR^4$, OH, $OR^4$, $OS(O)_nR^4$, $S(O)_nR^4$, $SO_2NR^5R^6$, $CONR^5R^6$, $NR^5R^6$, $NR^4SO_2R^5$, $NR^4CO_2R^6$, $NR^4COR^6$, $NR^4SO_2NR^5R^6$, $NHSO_2R^5$, $NHCO_2R^6$, $NHCOR^6$, $NHCONR^4$, $NHSO_2NR^5R^6$, aryl, heteroaryl, $C_2$-$C_6$ alkenyl, $C_2$-$C_6$ alkynyl, $C_3$-$C_8$cycloalkyl or $C_{1-6}$ alkyl, the latter four groups being optionally substituted by one or more substituents independently selected from halogen atoms, aryl, heteroaryl, $OR^8$, $NR^5R^6$ or $S(O)_nR^7$ where n=0, 1 or 2;

Preferably X is $S(O)_n$ where n is 0, 1 or 2; more preferably X is S.

Preferably $R^1$ is halogen or $NHCOR^6$. More preferably $R^1$ is fluoro or NHCOMe.

Preferably $R^2$ is $C_{1-7}$alkyl; more preferably $R^2$ is $C_{1-4}$alkyl, most preferably methyl.

Preferably $R^3$ is aryl optionally substituted by the groups defined above. More preferably $R^3$ is phenyl optionally substituted by the groups defined above. Most preferably $R^3$ is phenyl substituted by phenyl, or a 5-membered heteroaryl group, preferably oxazolyl.

Preferred compounds of the invention include:
[3-(Biphenyl-4-ylsulfanyl)-5-fluoro-2-methyl-indol-1-yl]-acetic acid;
[5-Fluoro-2-methyl-3-(4-oxazol-5-yl-phenylsulfanyl)-indol-1-yl]acetic acid;
[4-Acetylamino-3-(biphenyl-4-ylsulfanyl)-2-methyl-indol-1-yl]-acetic acid;
[4-Acetylamino-2-methyl-3-(4-oxazol-5-yl-phenylsulfanyl)-indol-1-yl]-acetic acid and pharmaceutically acceptable salts thereof.

Certain compounds of formula (I) are capable of existing in stereo isomeric forms. It will be understood that the invention encompasses all geometric and optical isomers of the compounds of formula (I) and mixtures thereof including racemates. Tautomers and mixtures thereof also form an aspect of the present invention.

The compound of formula (I) above may be converted to a pharmaceutically acceptable salt or solvate thereof, preferably a basic addition salt such as ammonium, sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

It will be appreciated by those skilled in the art that in the processes of the present invention certain functional groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Compounds of formula (I) in which X is S can be prepared as outlined in Scheme 1:

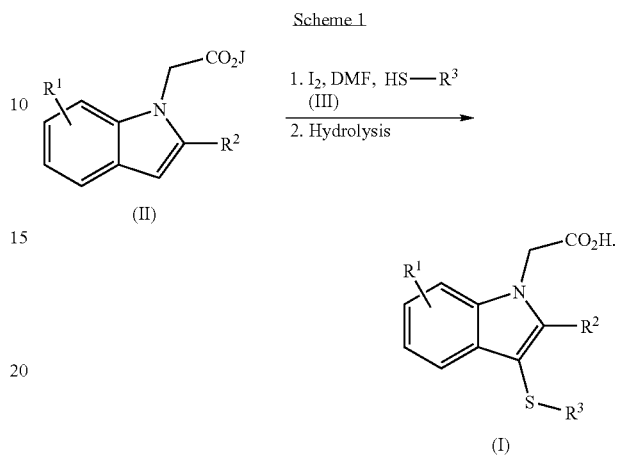

Scheme 1

In which $R^1$, $R^2$ and $R^3$ are as defined in formula (I) or are protected derivatives thereof. J is hydrogen or alkyl for example methyl, ethyl or tert-butyl. Iodine is added to compounds of formula (II) and formula (III) in a suitable solvent such as DMF at a suitable temperature such as room temperature. Where J is alkyl, hydrolysis of the resulting ester is carried out using standard conditions, for example where J is methyl or ethyl hydrolysis can be carried out using sodium hydroxide. Alternatively where J is hydrogen the sulfide formation can be carried out directly on an acid of formula (II) to give compounds of formula (I) without subsequent hydrolysis.

Compounds of formula (II) are commercially available or can be prepared by methods well known in the art or alternatively can be prepared using methods described in WO2003101961, WO2004007451, WO2004007452, WO2004106032, WO2005018529 and WO2005019171.

Compounds of formula (III) are commercially available or can be prepared by methods well known in the art.

The compounds of formula (I) or pharmaceutically acceptable salts thereof have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites.

A compound of the invention, or a pharmaceutically acceptable salt thereof, can be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, sclerodema, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

16. Diseases associated with raised levels of $PGD_2$ or its metabolites.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

In a further aspect, the present invention provides the use of a compound of formula (I), or a pharmaceutically acceptable salt or solvate thereof, as hereinbefore defined in the manufacture of a medicament for use in therapy.

In a further aspect, the present invention provides the use of a compound or formula (I), or a pharmaceutically acceptable salt or solvate thereof, as hereinbefore defined in the manufacture of a medicament for use in therapy in combination with drugs used to treat asthma and rhinitis (such as inhaled and oral steroids, inhaled β2-receptor agonists and oral leukotriene receptor antagonists).

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting α-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone faroate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2x7; or (xxvii) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The invention will now be illustrated by the following non-limiting examples in which, unless stated otherwise:

(i) the title and sub-titled compounds of the examples and methods were named using the ACD labs/name program (version 8.0) from Advanced Chemical Development Inc, Canada;

(ii) unless stated otherwise, reverse phase preparative HPLC (RPHPLC) was conducted using a Symmetry, NovaPak or Ex-Terra reverse phase silica column;

(iii) flash column chromatography refers to normal phase silica chromatography;

(iv) solvents were dried with $MgSO_4$ or $Na_2SO_4$;

(v) Evaporations were carried out by rotary evaporation in vacuo and work-up procedures were carried out after removal of residual solids such as drying agents by filtration;

(vi) Unless otherwise stated, operations were carried out at ambient temperature, that is in the range 10-40° C. and under an atmosphere of an inert gas such as argon or nitrogen;

(vii) yields are given for illustration only and are not necessarily the maximum attainable;

(viii) the structures of the end-products of formula (I) were confirmed by nuclear (generally proton) magnetic resonance (NMR) and mass spectral techniques; peak multiplicities are shown as follows: s, singlet; d, doublet; t, triplet; m, multiplet; br, broad; q, quartet, quin, quintet. $^1$H NMR data is quoted in the form of delta values for major diagnostic protons, given in parts per million (ppm) relative to tetramethylsilane (TMS) as an internal standard;

(ix) intermediates were characterised by thin layer chromatography (TLC), high-performance liquid chromatography (HPLC), mass spectrometry (MS), infra-red (IR) or NMR analysis;

(x) mass spectra (MS): generally only ions which indicate the parent mass are reported when given; MM=MultiMode;

(xi) the following abbreviations are used:

| EtOAc | Ethyl acetate |
|---|---|
| DMF | N,N-Dimethyl formamide |
| NMP | N-Methylpyrrolidinone |
| $MgSO_4$ | Magnesium sulphate |
| THF | Tetrahydrofuran |
| RT | Room temperature |

EXAMPLE 1

[3-(Biphenyl-4-ylsulfanyl)-5-fluoro-2-methyl-indol-1-yl]-acetic acid

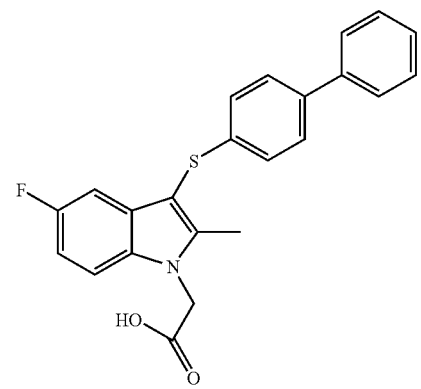

To a solution of (5-fluoro-2-methyl-indol-1-yl)-acetic acid (0.5 g) and biphenyl-4-thiol (0.19 g) in DMF (5 ml) was added iodine (0.25 g). After stirring at RT overnight the mixture was poured into water, the pH adjusted to 3 using 1M HCl and the organics extracted with EtOAc. The EtOAc extractions were combined, washed with brine, dried ($MgSO_4$) and evaporated under reduced pressure to give crude material. Purification using RPHPLC gave the title compound as a pink solid (0.1 µg).

MS: MM(−ve): 390.2 (M−H).

1H NMR (400 MHz, DMSO) δ 7.60-7.56 (m, 3H), 7.53-7.50 (m, 2H), 7.44-7.39 (m, 2H), 7.34-7.29 (m, 1H), 7.11-7.00 (m, 4H), 5.15 (s, 2H), 2.45 (s, 3H).

EXAMPLE 2

[5-Fluoro-2-methyl-3-(4-oxazol-5-yl-phenylsulfanyl)-indol-1-yl]acetic acid

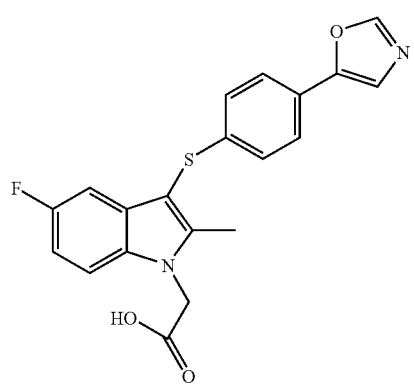

(i) 4-Oxazol-5-yl-benzenethiol

To a solution of 4-oxazol-5-yl-benzenesulfonyl chloride (1 g) in THF (20 ml) was added triphenylphosphine (4.3 g). After stirring at RT for 10 minutes water (2 ml) was added and the reaction was stirred for a further 20 minutes. The reaction was evaporated under reduced pressure and the residue dissolved in EtOAc. The EtOAc solution was extracted with 1M NaOH (×3), the basic extractions were combined, the pH adjusted to 3 using 1M HCl and then re-extracted with EtOAc (×3). The EtOAc fractions were combined and washed with brine, dried (MgSO$_4$) and evaporated under reduced pressure to give the subtitle compound as a green solid (0.65 g).

1H NMR (400 MHz, CDCL3) δ 7.90 (s, 1H), 7.54-7.50 (m, 2H), 7.34-7.31 (m, 3H), 3.53 (s, 1H).

(ii) [5-Fluoro-2-methyl-3-(4-oxazol-5-yl-phenylsulfanyl)-indol-1-yl]acetic acid The title compound was prepared by the method of example 1 using the product from step (i).

MS: MM(−ve): 381 (M−H).

1H NMR (400 MHz, DMSO) d 8.38 (s, 1H), 7.61-7.55 (m, 4H), 7.09-7.00 (m, 4H), 5.15 (s, 2H), 2.43 (s, 3H).

EXAMPLE 3

[4-Acetylamino-3-(biphenyl-4-ylsulfanyl)-2-methyl-indol-1-yl]-acetic acid

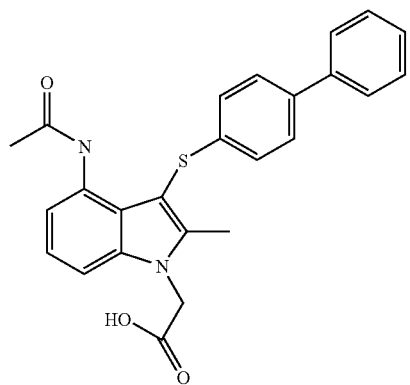

To a solution of (4-acetylamino-2-methyl-indol-1-yl)-acetic acid ethyl ester (0.27 g) and biphenyl-4-thiol (0.19 g) in DMF (5 ml) was added iodine (0.25 g). After stirring at RT overnight 1M NaOH (3 ml) was added and the reaction stirred at RT for a further 12 hours. The reaction was poured into water, the pH adjusted to 3 using 1M HCl and the organics extracted with EtOAc. The EtOAc extractions were combined, washed with brine, dried (MgSO$_4$) and evaporated under reduced pressure to give crude material. Purification using RPHPLC gave the title compound as a pink solid (0.16 g).

MS: MM(−ve): 429.2 (M−H).

1H NMR (400 MHz, DMSO) d 9.61 (s, 1H), 7.61-7.52 (m, 5H), 7.42 (t, J=7.6 Hz, 2H), 7.35-7.30 (m, 2H), 7.14-7.06 (m, 3H), 5.13 (s, 2H), 2.43 (s, 3H), 1.88 (s, 3H).

EXAMPLE 4

[4-Acetylamino-2-methyl-3-(4-oxazol-5-yl-phenylsulfanyl)-indol-1-yl]-acetic acid

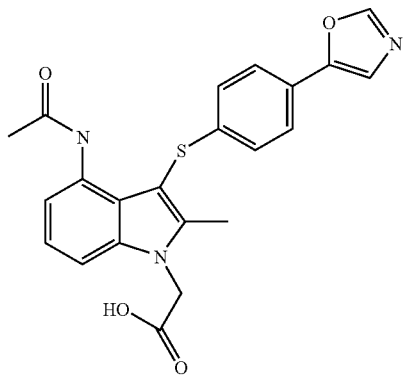

The title compound was prepared by the method of example 3 using (4-acetylamino-2-methyl-indol-1-yl)-acetic acid ethyl ester and the product of example 2 step (i).

MS: MM(+ve): 422 (M+H).

1H NMR (400 MHz, DMSO) d 9.53 (s, 1H), 8.38 (s, 1H), 7.59-7.54 (m, 3H), 7.49 (d, J=7.2 Hz, 1H), 7.22 (d, J=8.2 Hz, 1H), 7.11-7.03 (m, 3H), 4.74 (s, 2H), 2.39 (s, 3H), 1.85 (s, 3H).

Pharmacological Data

Ligand Binding Assay

[$^3$H]PGD$_2$ was purchased from Perkin Elmer Life Sciences with a specific activity of 100-210 Ci/mmol. All other chemicals were of analytical grade.

HEK cells expressing rhCRTh2/Gα16 were routinely maintained in DMEM containing 10% Foetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 0.1 mM dithiothreitol, 1 mM EDTA, 0.1 mM phenyl methyl sulphonyl fluoride and 100 μg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C. The final pellet was re-suspended in 4 ml of membrane homogenisation buffer per cell factory used and the protein content determined. Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 μg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 µl of 6.25 nM [$^3$H]PGD$_2$, 20 µl membrane saturated SPA beads both in assay buffer and 10 µl of compound solution or 13,14-dihydro-15-keto prostaglandin D$_2$ (DK-PGD$_2$, for determination of non-specific binding, Cayman chemical company).

Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at RT for 2 hours and counted on a Wallac Microbeta liquid scintillation counter (1 minute per well).

Compounds of formula (I) have an IC$_{50}$ value of less than (<) 10 µM. Specifically example 1 has a pIC50 of 7.7.

The invention claimed is:

1. A compound of formula (I) or a pharmaceutically acceptable salt thereof:

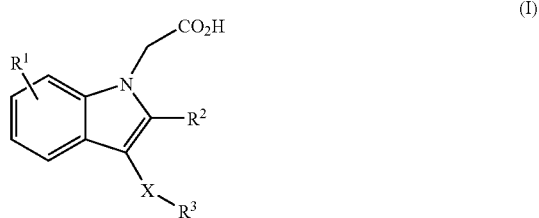

(I)

in which
X is O or S;
R$^1$ is NHCOR$^6$;
R$^2$ is hydrogen, halogen, or C$_{1-7}$alkyl;
R$^3$ is phenyl, which is substituted by phenyl; or phenyl, which is substituted by a 5-membered heteroaryl group;
R$^6$ is a hydrogen atom, or C$_{1-6}$alkyl;
Provided that:
R$^3$ cannot be 4-phenyl-1,3-thiazol-2-yl.

2. The compound or salt according to claim 1 where X is S.

3. The compound or salt according to claim 1 where R$^2$ is C$_{1-7}$alkyl.

4. The compound or salt according to claim 1 where R$^2$ is methyl.

5. The compound or salt according to claim 1 where R$^3$ is phenyl substituted with phenyl; or phenyl substituted with oxazolyl.

6. The A compound or salt according to claim 1 or claim 3 selected from:
[4-Acetylamino-3-(biphenyl-4-ylsulfanyl)-2-methyl-indol-1-yl]-acetic acid; and
[4-Acetylamino-2-methyl-3-(4-oxazol-5-yl-phenylsulfanyl)-indol-1-yl]-acetic acid;
or a pharmaceutically acceptable salt thereof.

7. A pharmaceutical composition comprising a compound of formula (I) or a pharmaceutically acceptable salt thereof, as claimed in claim 1, in association with a pharmaceutically acceptable adjuvant, diluent, or carrier.

8. A method of treating asthma in a patient suffering from asthma, which comprises administering to the patient a therapeutically effective amount of a compound of formula (I) or a pharmaceutically acceptable salt thereof, as claimed in claim 1.

9. A method of treating rhinitis in a patient suffering from rhinitis, which comprises administering to the patient a therapeutically effective amount of a compound of formula (I) or a pharmaceutically acceptable salt thereof, as claimed in claim 1.

10. The compound or salt according to claim 3 where X is S.

11. The compound or salt according to claim 3 where R$^2$ is methyl.

12. The compound or salt according to claim 3 where R$^3$ is phenyl substituted with phenyl; or phenyl substituted with oxazolyl.

13. A pharmaceutical composition comprising a compound of formula (I) or a pharmaceutically acceptable salt thereof, as claimed in claim 3, in association with a pharmaceutically acceptable adjuvant, diluent, or carrier.

14. A method of treating asthma in a patient suffering from asthma, which comprises administering to the patient a therapeutically effective amount of a compound of formula (I) or a pharmaceutically acceptable salt thereof, as claimed in claim 3.

15. A method of treating rhinitis in a patient suffering from rhinitis, which comprises administering to the patient a therapeutically effective amount of a compound of formula (I) or a pharmaceutically acceptable salt thereof, as claimed in claim 3.

* * * * *